United States Patent [19]

Ginsberg et al.

[11] 4,234,538
[45] Nov. 18, 1980

[54] APPARATUS FOR MONITORING CHEMICAL REACTIONS AND EMPLOYING MOVING PHOTOMETER MEANS

[75] Inventors: Guenter Ginsberg, Miami, Fla.; Thomas Horne, Harpenden, England; Robert L. Kreiselman, Miami, Fla.

[73] Assignee: Coulter Electronics, Inc., Hialeah, Fla.

[21] Appl. No.: 846,337

[22] Filed: Oct. 28, 1977

Related U.S. Application Data

[63] Continuation-in-part of Ser. No. 808,168, Jun. 20, 1977, abandoned.

[51] Int. Cl.$^2$ .................. G01N 21/24; G01N 1/14
[52] U.S. Cl. ........................ 422/64; 250/208; 356/246; 356/435; 356/222; 422/67
[58] Field of Search ............. 23/230 R, 253 R, 259; 422/64, 67; 356/435, 246, 436; 250/565, 208

[56] References Cited

U.S. PATENT DOCUMENTS

| | | | |
|---|---|---|---|
| 3,504,981 | 4/1970 | Malvin | 356/185 |
| 3,554,654 | 1/1971 | Paatzsch et al. | 356/180 |
| 3,567,393 | 3/1971 | Welch | 23/253 R |
| 3,748,044 | 7/1973 | Liston | 23/253 R X |
| 3,873,273 | 3/1975 | Moran et al. | 23/253 R |
| 4,007,011 | 2/1977 | Greaves et al. | 23/259 |

FOREIGN PATENT DOCUMENTS 844876 12/1976 Belgium.
905301 9/1962 United Kingdom.
1192008 5/1970 United Kingdom.

OTHER PUBLICATIONS

Anderson, Analytical Biochemistry, 28, 545-562, (1969).

*Primary Examiner*—R. E. Serwin
*Attorney, Agent, or Firm*—Silverman, Cass & Singer, Ltd.

[57] ABSTRACT

Apparatus for measuring progressively the absorbance changes of a large number of aliquots from a plurality of different samples. The sample introduction, testing instructions, aliquot preparation, reagent dispensing, absorbance measuring and data recording all can be accomplished in a continuous mode of processing. Stat and batch operation also can be accomplished. The aliquots are in an array of cuvettes which is advanced slowly along a circular path. Photometer means, preferably having several photometric detectors, are mounted in fixed orientation on a common support that advances rapidly along a similar circular path, such that radiation passing through each of the cuvettes is monitored many times by a specific photometric detector by the time that that cuvette completes one circuit of its path. The photometric detectors can operate at several different wavelengths. Many different chemical reactions can be monitored at the same time. The radiant energy passing through each cuvette is received by the continuously moving photometer means, is converted electrically into a digitized value proportional to absorbance and is transmitted digitally from the moving assemblage of photometric detectors, cuvettes and electrical components to a stationary receiver. In one embodiment, the digital transmission is in the form of a pulsed train of light signals. In another embodiment, one or more slip rings transmit electric signals from the moving assemblage to the stationary portion. Suitable drive elements, sample and reagent storage and transfer mechanisms as well as cuvette laundry means may be provided as part of the complete apparatus.

12 Claims, 16 Drawing Figures

APPARATUS FOR MONITORING CHEMICAL REACTIONS AND EMPLOYING MOVING PHOTOMETER MEANS

CROSS REFERENCE TO RELATED APPLICATION

This is a continuation-in-part of our application of the same title Ser. No. 808,166 filed June 20, 1977, now abandoned.

BACKGROUND OF THE INVENTION

This invention relates to apparatus for monitoring repeatedly the absorption of electromagnetic radiation by a plurality of specimens occurring during a period of time. More particularly, this invention concerns an apparatus by which each of a plurality of samples provides a plurality of aliquots which can be subjected to chemical reaction with different reagents. The absorbance of each aliquot repeatedly is measured during a predetermined reaction time. The inputting of the samples, obtaining their aliquots, selecting and adding of reagents, and the absorbance measuring all can be effected in a continuous mode as well as a stat and a batch mode of operation. The term "aliquot" as employed herein is a noun meaning a portion of a sample.

Apparatus described hereinafter would be well suited for the measurement of kinetic reactions such as useful in enzyme analysis as well as end point measurement. Many chemical reactions require from a few seconds to many minutes to be completed and, during such kinetic reaction time, it is often important to observe the progress of the reaction by making measurements several times. One form of measurement is ascertaining the absorbance of electromagnetic radiation of a particular wavelength by the analyte. Typically, enzyme reaction measurements have been accomplished by batch handling methods and apparatuses requiring a considerable amount of preparation and manipulation by the laboratory technician. The nature of the process cannot help but result in relatively low throughput. Examples of batch operating enzyme analyzers are disclosed in Wood et al U.S. Pat. No. 3,344,702 and Liston U.S. Pat. No. 3,748,044, the latter having automated the aliquot preparation and reagent dispensing, but being limited to a single chemistry determination for all of the aliquots in the batch being processed.

In contrast to the batch mode a more efficient method is the continuous mode in which the apparatus can remain operating as long as there are samples to be tested, with old samples and their tested aliquots being "replaced" by new samples and their aliquots without interruption of the operation of the testing apparatus. Such continuous operation is well known in biological chemistry testing systems and is taught, for example, in Jones U.S. Pat. No. 3,799,744 and Hoskins et al U.S. Pat. No. 3,883,305, in which separate chemistry tests can be made for several different aliquots from the same sample.

A disadvantage of such systems is that they are capable of making only a single photometric measurement on a given aliquot and even if an attempt is made to achieve measurement of kinetic reaction by, for example two time-separated measurements, these must be effected on different aliquots of the same sample. Thus, these systems are not designed to measure kinetic reactions by multiple point observations on a single aliquot.

Recently published Greaves et al U.S. Pat. No. 3,966,322 discloses a specimen investigating apparatus suitable for measuring kinetic reactions in a continuous operations mode. Greaves et al teaches that illumination of the plurality of specimens, which are circumferentially mounted in cuvettes around the periphery of a turntable, originates from a single non-rotating light source that projects a beam of light vertically down the axis of the hollow shaft of the turntable. Optical elements then divert and direct the light beam radially outward toward one of the specimen holding cuvettes and to a radially inwardly reflected or directed return path that terminates with a vertically down-the-axis output to a fixed light detector. The optical elements providing this tortuous path for the light beam are mounted for rotation around the same axis but at a higher speed than the specimen turntable. With only one light source and one optical train, only one specimen can be monitored at any one instant and each specimen is monitored only once per revolution of the optical train.

Greaves et al as well as another apparatus which has been described recently that is similar to Greaves et al has two disadvantages. The light source for this type of device comprises a tungsten or similar lamp having a filament. The light source remains fixed while the optical elements of the train rotate. The orientation of the lamp filament with respect to the optical elements of the train will change with rotation, exacerbated by precession and the intersection of the light beam with the photodetector at the end of the long optical path will change similarly. The obvious sources of error then become the following:

(1) The light input varies because light emitted from different parts of the lamp filament is nonuniform and the optical elements of the train look at different parts of the filament at different times.
(2) The output from the photodetector varies because it has different response in different areas of its sensitive surface and the incident energy beam impinges varying areas of this surface at different times.

Another prior art device is disclosed in DeMendez et al U.S. Pat. No. 3,829,221 in which a single light source and photoresponsive detector rotate in unison. The cuvettes are necessarily stationary. This enables only batch methods of measurement of absorbance using a single wavelength.

SUMMARY OF THE INVENTION

The present invention seeks to reduce the limitations found in the prior art, while at the same time to provide increased measuring accuracy and testing versatility, especially for monitoring kinetic reactions. Apparatus is provided which operates in the continuous mode and in which photometer means preferably comprising a plurality of photometric detectors, (but which can comprise a single photometer) continuously scan an array of cuvettes that is being indexed at a slower speed around a preferably circular path. As employed herein, "index" is a verb which encompasses both stepping and continuous or smooth movement.

In one embodiment, the photometer means include a plurality of radiation sources and radiation detectors of the photoresponsive type that are respectively mated. Each source is aligned with its associated detector in a fixed orientation that is maintained at all times during rotation of the rotor which carries the photometer means, the axis of alignment lying on a radius of the rotor and also lying on a radius of a cuvette-carrying turntable that is mounted for rotation coaxial with the rotor. The axis of alignment is such as to intersect a circular array of circumferentially arranged cuvettes mounted on the turntable, there being a clear space between each source and its associated detector through which the circular array of cuvettes passes without mechanical interference.

In another embodiment, the photometer means comprise a single rotating radiation source in the center of the rotor which radiates its beams of radiation to an array of axially arranged detectors spaced around the rotor. The photometer means define radial optical trains including a clear area, these trains sweep circular areas concentric with the array of cuvettes carried by the turntable about the axis where the single light source is positioned. The cuvettes pass through the clear area of each train; the alignment of the light source relative to its associated detector never changes because the light source is fixed relative to all of the optical trains. On this account during one rotation of the rotor and its detectors there will be a plurality of scannings of each cuvette, specifically, each of the photometers will scan every cuvette. For example, if there are eight photometric detectors each cuvette will be scanned eight times and there will be provided eight measurements of absorbance. This, of course is true for both of the embodiments mentioned, that is, where there is a single light source or a plurality thereof. The cuvette turntable will normally be moving at a very slow speed, enabling the aliquots to be loaded and unloaded continuously, say of the order of a fraction of a revolution a minute. The rotor carrying the photometer means on the other hand will be rotating at a relatively higher speed, say of the order of 500 to 1000 revolutions per minute. The amount of information which can be gathered in a very short time is clearly quite voluminous. When it is appreciated that the photometric detectors are preferably operated at different wave lengths, for example by using different filters in their respective optical trains, then it becomes clear that not only is the quantity of information gathered voluminous but that information is made up of many different kinds.

The movement of the rotor is continuous while the movement of the turntable is preferably intermittent, that is, indexed. The apparatus is programmed in such case, by suitable electronic circuitry, to make the measurements of absorbance while the cuvettes are not moving but are in a dwell period. This is more easily accomplished than attempting to have the turntable moving at a continuous slow speed and programming the photometers to do their scanning for short periods of time while the cuvettes are aligned with the respective photometer trains during rotation. The invention, however, includes a structure of this latter type.

Where the materials comprising the samples to be measured by the apparatus comprise sources of radiation in and of themselves, being luminescent, fluorescent or radioactive, the light source is not required. The source in such case may be turned off or blocked.

The amount of radiation transmitted by each specimen or aliquot carried in the cuvettes is detected on each scan and is converted into a digital value proportional to absorbance by means of an electrical circuit which includes an A/D converter. The A/D converter of each photodetector is carried by the rotor itself adjacent to the photodetector thereby economizing in connections and rendering transmission from the moving rotor to the fixed portion of the apparatus relatively simple. The digital value is transmitted from the photometer rotor by suitable means coupling the rotating part with the fixed part of the apparatus. One embodiment includes a light emitting diode and another has slipring means. The signals are transmitted to a receiver which is stationary and thence to suitable storage or processing means. For example, the signals may pass first to a console where they receive routing information from a master control unit that governs the programming and operation of the entire apparatus.

The apparatus is arranged to provide end point information as well as information on kinetic reactions.

The invention has an important advantage in that the relationship between the light source and photodetector in every case is geometrically fixed so that there can be no variation during rotation of the rotor. Since the turntable of cuvettes is mounted on the same axis any slight eccentricity which exists by reason of construction or develops during use has no practical effect on measurements made.

DESCRIPTION OF THE PREFERRED EMBODIMENT

Figure 1:
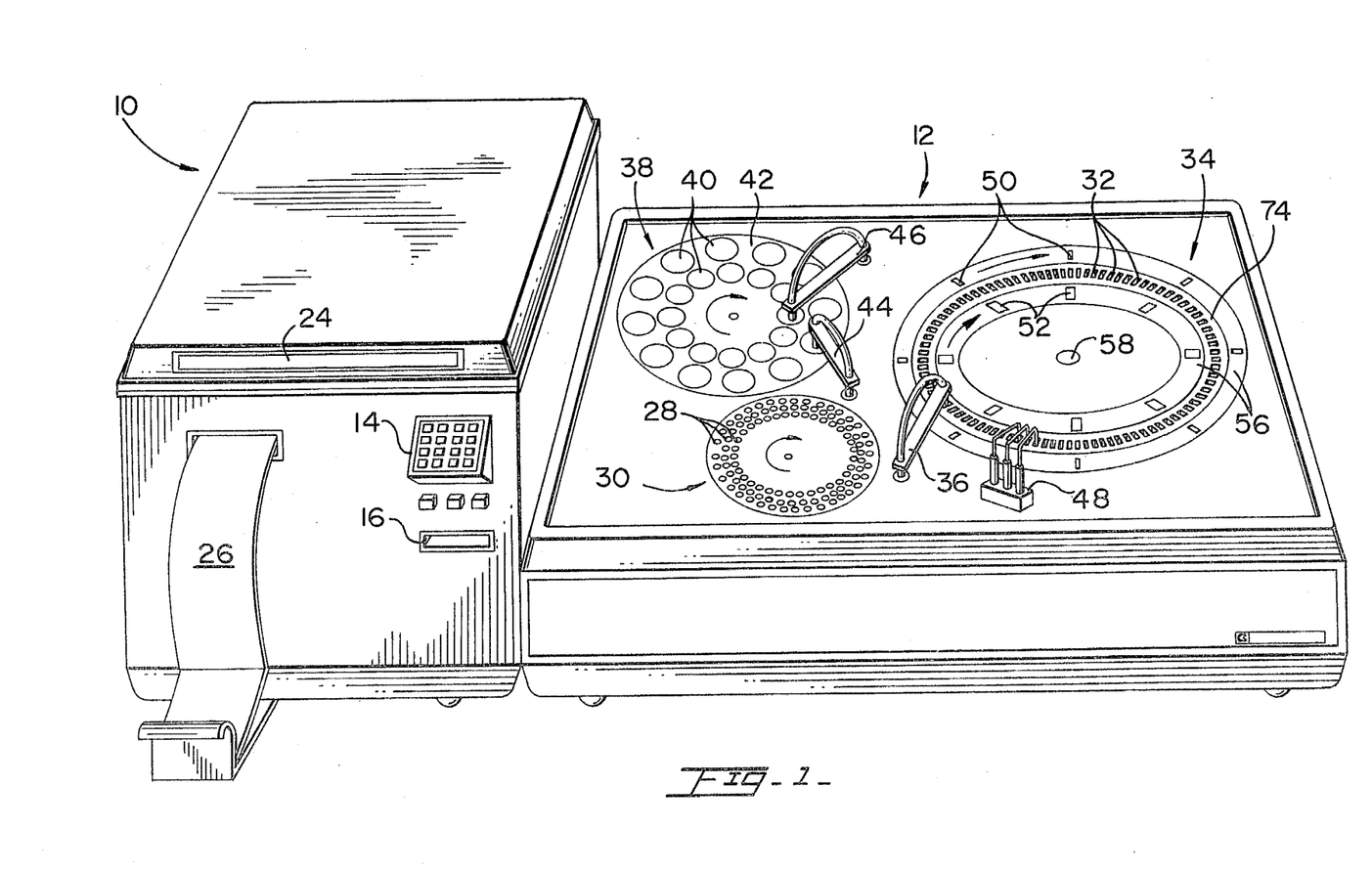
FIG. 1 is a perspective somewhat diagrammatic view of one embodiment of the complete apparatus of the invention.
Figure 5:
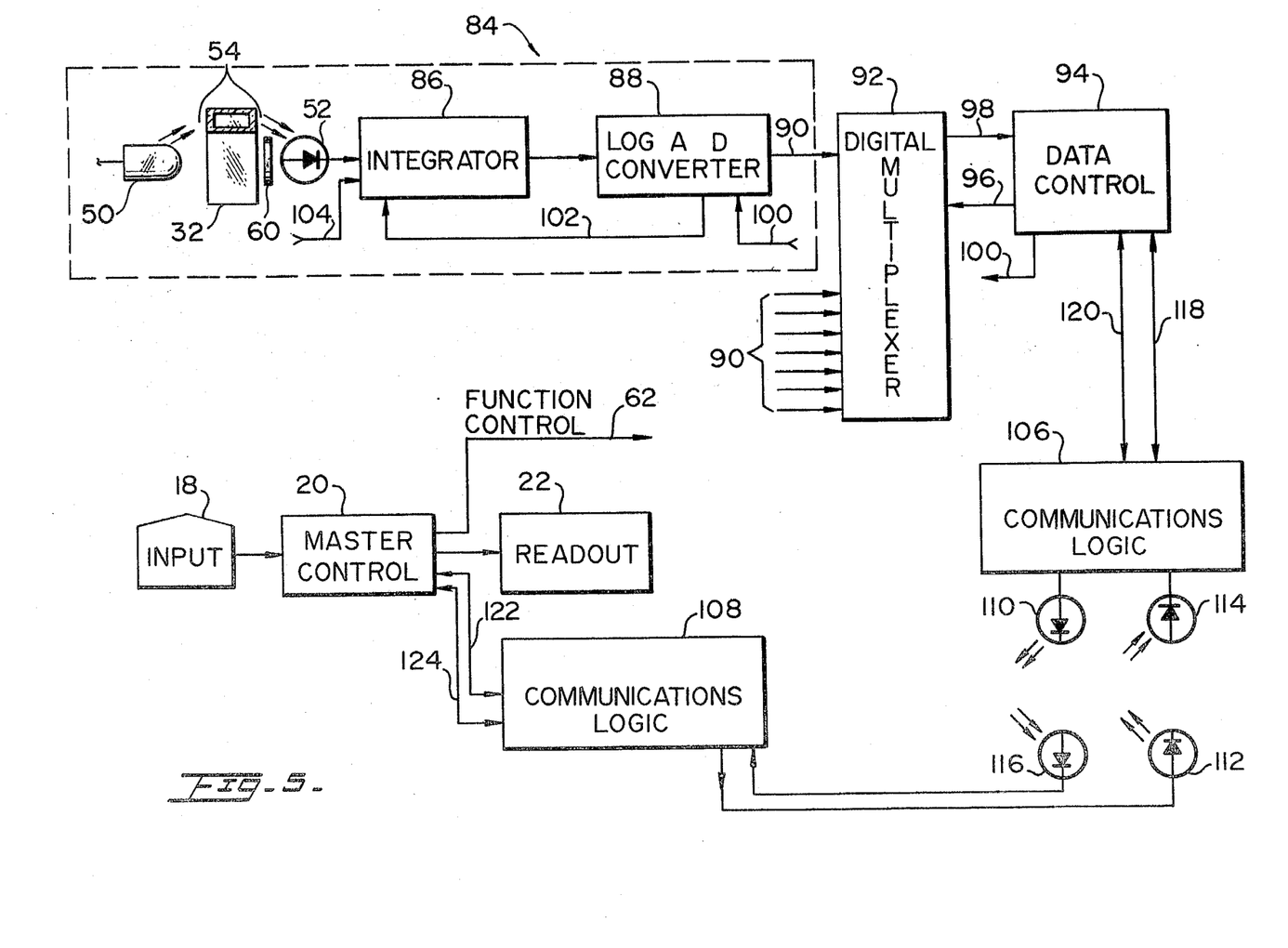
FIG. 5 is an electrical block diagram primarily of the portions of the apparatus concerned with the generation and transmission of digitized absorbance data.

With reference to FIGS. 1 and 5 which are somewhat diagrammatic, the subject apparatus can be composed of a control console 10 and a chemistry processing portion 12. Input information, concerning each sample and the different chemical tests to be performed on aliquots of each specific sample, can be supplied by way of a keyboard 14 and/or data cards fed into a receiver 16 of suitable data input means 18. The input information then is applied to a master control unit 20, which has many functions, only some of which will be mentioned hereinafter, but those skilled in the art will appreciate the more complete control ambit of this unit. A first function of the master control unit 20 can be to feed the input information to a readout unit 22, which can include a visual display 24 and a printer of a tape 26, from which the operator can verify that the input information has been entered accurately.

The master control unit 20 can store a list of commands pertinent to each of the chemistry tests that the apparatus is capable of performing. Thus, when the input information associates a specific sample with a specific set of tests, and assuming the apparatus has needed diluent and reagents, all that remains to be accomplished by the human operator is to have placed the sample into an appropriate one of the sample holders 28 in a sample disc 30. Thereupon, the master control unit 20 can control the transferring of sample aliquots into cuvettes 32 mounted in an annular array in a turntable which is part of the data generating portion 34. An aliquot and diluent transfer mechanism 36, forms of which are known, can accomplish the transferring, with each required chemistry test being associated with an identified cuvette 32 for that specific sample. As the several aliquots are being dispensed, the cuvette array will be indexed forward one step for each cuvette and its associated aliquot. As used herein, "step" and "indexed" include but are not limited to discrete movements, since the cuvette array could be continuously moving slowly.

A reagent supply area 38 has separate reagent containers 40 in a reagent disc 42. First and second reagent dispensers 44 and 46 will add appropriate reagents to specific cuvettes as those cuvettes advance around the path of movement of the annular array. The dispensing point of the first reagent dispenser relative to the cuvette path is spaced several steps prior to that of the second dispenser 46 so that in this space interval, which corresponds to a known time interval, the first reagent can have reacted with an aliquot prior to the introduction of the second reagent. Some chemical tests may require the addition of reagent from only one of the dispensers.

The aliquot and diluent transfer mechanism 36 as well as the reagent dispensers 44 and 46 can be of the type and operate as disclosed with reference to FIGS. 13c and 16 of U.S. Pat. No. 3,883,305 entitled Automatic Chemical Analysis Apparatus and assigned to the assignee of the present invention. Such transfer dispensers would swing arcuately between the source of fluid 28 or 40 and a cuvette 32. Both when receiving and dispensing fluid the probe of the dispensers can move down into the vessels 28, 32 and 40, but would be elevated to be able to swing free thereof in an arcuate path.

Between the time and position that the aliquot is dispensed and the first reagent is dispensed there is a distance along the path of the cuvettes during which measurement of the transmittance of the aliquot with its diluent and the cuvette walls can be accomplished. Just prior to the point that each cuvette is again being positioned beneath the aliquot dispenser mechanism 36 there is a laundry station 48 having probes and mechanisms for removing the reactants, if any, from the cuvette, washing the cuvette and making it usable for receipt of a new aliquot. The laundry station can be similar to that disclosed with reference to FIG. 16 of U.S. Pat. No. 3,883,305.

Figure 2:
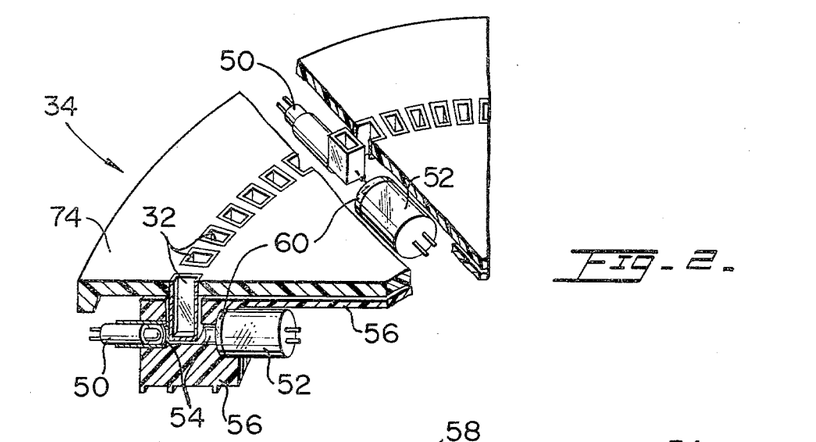
FIG. 2 is a fragmentary perspective view of the cuvette turntable and the photometer rotor illustrating one embodiment of the photometer means, portions being shown in section and other portions being broken away.
Figure 3:
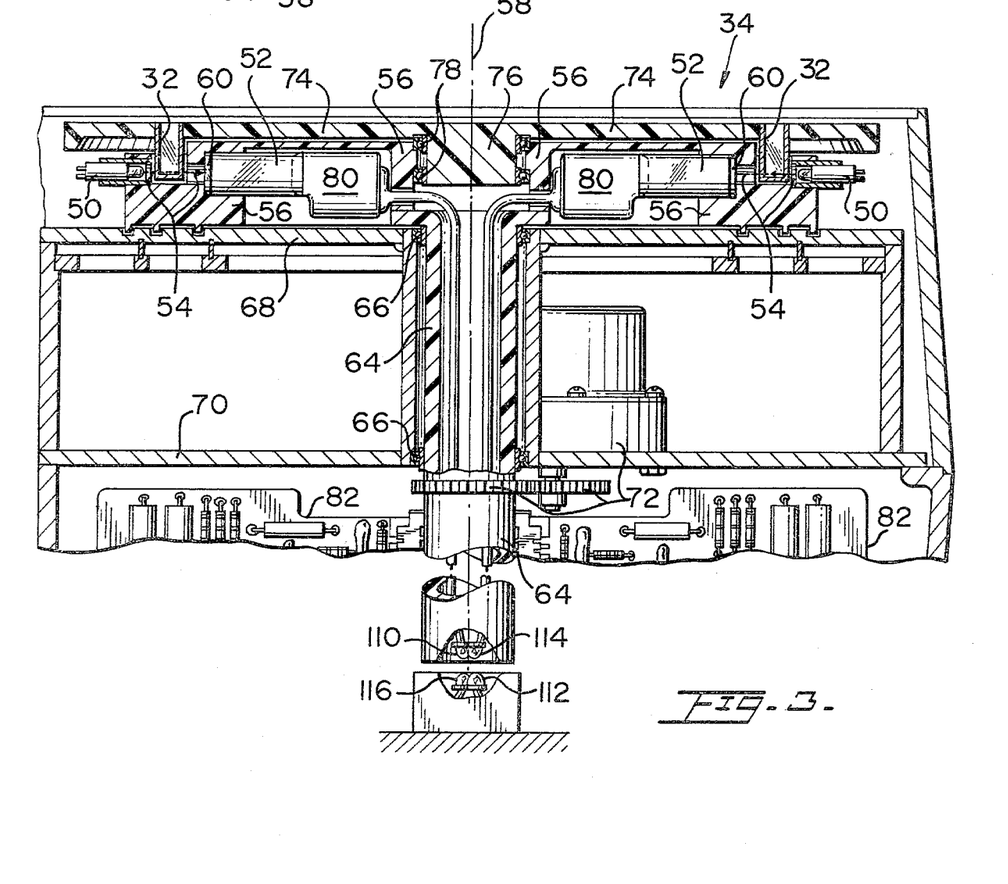
FIG. 3 is a median fragmentary sectional view through the data generating components of the apparatus further detailing the embodiment of FIG. 2.

The data-generating means 34 are characterized by the presence of a plurality of photodetectors radially arranged around a rotor 56 and comprising a source of radiation such as a lamp 50 and individual radiation detectors 52 which can be photoelectric cells, photomultipliers or the like. Each detector 52 may have its own light source 50 as shown in the embodiments of FIGS. 2 and 3 or there may be a single light source such as the lamp 50 in the embodiment of FIG. 4. (The same reference numerals are applied to the same or equivalent components in the two embodiments).

Figure 4:
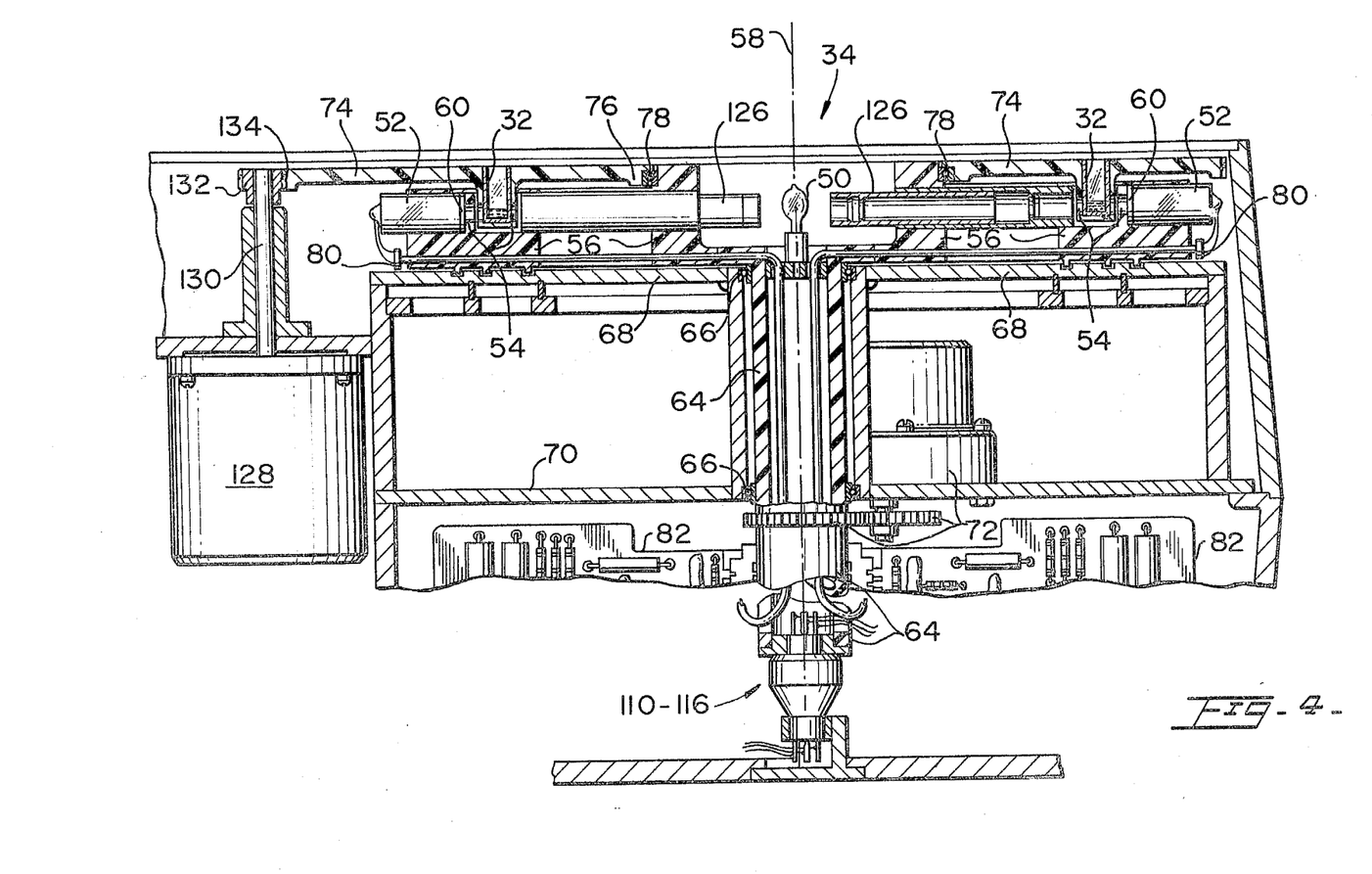
FIG. 4 is a view similar to that of FIG. 3, but detailing a second embodiment of the photometer means and a second embodiment of the data transmission arrangement.

In the first embodiment the individual lamps 50 are located outboard of the path followed by the circular array of cuvettes, while in the second embodiment the single lamp 50 is located at the axis of the rotor 56.

In both embodiments the photodetector means are wholly carried by the rotor 56 insofar as the source and detector 52 are concerned. The radiation paths 54 in all events are substantially shorter than that of the Greaves et al patent above-mentioned because each path of FIGS. 2, 3 and 4 is direct and has no bends produced either by mirrors, prisms or fiber-optic elements. Such path will always be at most about the radius of the rotor 56 and usually, as for example in the embodiment of FIGS. 2 and 3, a fraction of the rotor radius. Thus, the path is a few centimeters long and has the barest minimum of optical elements in the train. No matter how well constructed optical elements are, their slight inaccuracies, aberrations, light refractions and scattering are cumulative so that long trains like those of Greaves et al lose and absorb radiant energy during passage decreasing the available signal to noise ratio in making photometric measurements.

The advantages of the invention are principally derived where there is a plurality of photometers mounted on the rotor 56 but some of the advantages of the invention are available if only one photometer is utilized; hence reference to "photometer means" is intended to encompass both concepts. It is clear that in a single photometer as compared with a rotor having eight photometers the rate at which data can be gathered would be less for the single photometer than for the multiple photometer device, assuming that the number of cuvettes in the turntable and the speed of rotation of the rotor are the same in both cases. A single photometer apparatus can have its rate of data generation increased by increasing its speed of rotation. The capacity of data handling, storage and so on of the data processing means will be dependent upon the amount of data being generated. Likewise the complexity of the data processing means will be related to the variety of data generated. All of these factors and more come into play in the choice of the number of photometers, the speed of the rotor, the wavelengths at which measurements are made, and the chemical reactions which can be handled by the apparatus.

For comparison purposes it is pointed out that the scale of the drawings in FIGS. 2 to 4 is such that the diameter of the rotor 56 measured below the location of the lamps 50 in FIG. 3 is approximately 30 centimeters so that the total optical path from lamp 50 to the photoresponsive device is less than about 2 centimeters in the embodiments of FIGS. 2 and 3 and less than about 8 centimeters in the embodiment of FIG. 4.

The circle of cuvettes 32 carried on the disc or turntable 74 rotates on the axis 58 which is also the axis of rotation of the rotor 56. Thus, the cuvette array and the photometers are concentric. The mounting and driving means for the rotor 56 and the turntable 74 will be detailed with reference to FIGS. 2 to 4; however operational, timing and position relationships can be considered with reference to FIG. 1. As mentioned above, the rotor 56 in FIGS. 2 to 4 may be considered to have a diameter of about 30 centimeters which indicates a scale of roughly half-size in those Figures. FIG. 1 is illustrated at about one-fifth full size. In neither case is this intended to be limiting since the invention has broad application to many different forms and sizes of apparatus.

It will be apparent from the foregoing that during its complete circuit of movement for a single revolution of the turntable 74 any given cuvette 32 will have had its aliquot subjected to fluid processing, chemical reaction and measurement, and as well will be prepared to receive a new aliquot for the repetition of the cycle. The path of the cuvettes is a circle in the apparatus which has been illustrated and will be described as such, but modified forms of the invention may vary this.

The turntable 74 will be indexed at a relatively slow rate, making a total of about five to twenty revolutions per hour, with the periods of dwell somewhat longer than the periods of movement. This speed is said to be relatively slow in contrast to the speed of the rotor 56 with its photometers which will be normally rotating at a speed of as much as several hundred revolutions per minute. Thus, for each dwell period, at which time the measurements are preferably programmed to be taken, there can be many rotations of the rotor taking place with the corresponding number of measurements being made by all photometers of all cuvettes. Preferably there should be a minimum of one revolution of rotor 56 per dwell period.

In this way, many time spaced photometric measurements of the reaction in any specific cuvette can be made, recorded and/or stored for data processing in a single circuit of the cuvette path, that is, during one revolution of the turntable 74. The described mode of processing and endpoint determination can readily be effected in this period of time, not only for the aliquot in the single cuvette 32 but for a continuous number of aliquots being added to and removed from the cuvettes 32 of the turntable 74.

If there are 120 cuvettes 32 mounted on the turntable 74 and the turntable is indexed once every six seconds, one full circuit is achieved as a single revolution of the turntable 74 relative to the housing carrying the data generating components 34 every twelve minutes. If the rotor 56 and its eight photometers rotate around the axis 58 at a speed of one revolution every six seconds, this is a relatively slow speed of ten revolutions per minute or 120 revolutions of the rotor 56 for each revolution of the turntable 74. If we assume that measurements are being made at all times, each cuvette 32 of the array on the turntable 74 will be scanned photometrically 960 times in a complete circuit relative to the housing carrying the data generating components, for example, relative to the point where the aliquot has been inserted. If the speed of the rotor 56 is doubled the number of measurements will increase to 1920 times, but it should be appreciated that since this is for only one cuvette and its aliquot, the total number of measurements made in a single revolution of the turntable 74 is of the order of 18,000 for the slower speed of the rotor 56 and 36,000 for the double speed mentioned.

Since some of the positions where cuvettes 32 will be located will be employed for laundering the cuvettes, some will be employed for injecting the aliquot and carrying the same to the reagent insertion location and some may even be employed for agitation, the total number of cuvette positions around the circular path where the measurement or monitoring is taking place may be less than the total number of cuvettes. Thus the total number of measurements mentioned above may be less than stated by an amount which takes into account the locations needed for the above-mentioned functions. It might be mentioned that monitoring may be continued at every position, if desired, leaving the data processing control means to discard readings which have no significance. Readings made during periods where laundering is taking place could be equated to blank measurements and even some information can be acquired from the aliquot in non-reactive condition before the introduction of reagents. For the purposes of the discussion which follows, it will be assumed that 800 separate photometric measurements can be made on each aliquot where the rotor is rotating at ten revolutions per minute, there are 120 cuvettes, the indexing is taking place at a rate of one revolution of the turntable 74 in twelve minutes, each step of the indexing occurs every 6 seconds and there are several stations along the path of the cuvette array which are occupied by functions that are not concerned with photometric monitoring.

Since 800 measurement points of a reaction, each measurement being three-fourths of a second apart during ten minutes, may not be required and since certain chemical tests can be monitored better at a specific wavelength, each of the photometers can be provided with a specific filter 60 so that each photometer can produce radiation and make measurements at its own wavelength. Assuming that each of the filters 60 is different and information from a specific aliquot in a specific cuvette most valuably can be obtained from only one of the eight photometers, then there can be obtained from such one photometer one hundred measurements of the reaction of that one aliquot during the ten minute cycle because there is one measurement every six seconds. Certainly, if it is desired that a reaction be monitored more often than once every six seconds, more than one of the photometers can be constructed to operate at the same wavelength.

It is pointed out that the photometers which are illustrated in the drawings are equally spaced around the rotor 56, but other arrangements where the photometers are grouped or spaced unequally are encompassed by the scope of the invention. Bichromatic determinations may be desirable in pairs of photometers very closely spaced.

As known, with the proper choice of reagents, several different reactions can be monitored at the same wavelength; hence, with a capability of several different wavelengths and suitable reagent selection, numerous different tests can be processed by the apparatus. Since all of the cuvettes are being scanned by each of the photometers, the availability of different photometers monitoring at different wavelengths permits aliquot alone as well as a reaction in a cuvette to be monitored by more than one photometer and therefore at more than one wavelength, with the separation of time between monitoring at different wavelengths being three-fourths of a second in the illustrated embodiment. It will of course vary pursuant to construction and requirements. Each aliquot need not be monitored at all wavelengths, nor does each sample have to provide aliquots for all tests capable of being achieved by use of the apparatus. The data into the input means 18 and the master control unit 20 can be controlled and programmed in such a manner as to command the execution of only those tests requested for each sample and will employ cuvettes only as needed, thereby reducing the total amount required of sample and reagent volumes and maximize the utilization of the cuvette positions and the photometer means to maximize sample throughput of the apparatus.

The apparatus does not require a fixed set of several tests for each sample even if different ones of the set of tests would not be requested for certain of the samples nor, as is also well known in the prior art, does the apparatus cause empty cuvettes representing "skipped" tests to occupy space in the rotating array on the turntable 74. The just mentioned and other sample processing control functions by the master control unit are carried on a function control bus 62, shown in FIG. 5.

It will be mentioned at this point by way of recapitulation and emphasis that the apparatus of the invention has great flexibility in being applicable to many choices of testing but without sacrificing economy or throughput. As mentioned above, each aliquot need not be monitored on all wave lengths. In addition to this, each sample does not have to provide aliquots for all tests capable of being accomplished by the apparatus. Test selection is here achieved without loss of analytical capacity, without wasting any of the aliquots or reagents, without carrying out any unnecessary tests whose data are useless and without skipping any cuvettes. On this account it can be appreciated that the throughput of the apparatus is also not affected by the great versatility of the device.

It may be said of this apparatus that it has true test selectivity without the equivocation of prior automatic chemistry devices in that if a test is not performed in a given cuvette that same cuvette is available for another test.

Next, with reference to FIGS. 2 and 3, the details of one embodiment of the data generating component assembly 34 will be discussed, with some reference also to FIG. 4. As shown, each radiation source 50 and its associated detector 52 are relatively close together and on a line and securely mounted to the rotor 56 and thereby define therebetween the short radiation path 54 of fixed length which lies on a radius from the axis 58. The rotor 56 is arranged to rotate on the axis 58 and is provided with a depending rotary sleeve 64 which is journaled on bearings 66 mounted to the housing base members 68 and 70. Suitable drive means 72 can be be coupled to the sleeve 64 to apply the rotational movement to the rotor 56 and its photometers, two of which are illustrated in FIG. 3. The photometer components and the short radiation paths 54 therebetween are thus held in fixed orientation with respect to each other and their radial orientation with respect to the axis 58. The journalled mounting of the support 56 provides a precision orientation of the radiation path 54 with respect to its distance from the axis 58, such distance remaining substantially constant as the rotor 56 is rotated.

The bearings 66 can be of any suitable conventional design and construction. The criteria for such bearings are accuracy, smoothness, reliability, in addition to providing the thrust support needed in view of the weight of the rotor 56 and its components. Radial support requirements in view of the weight and forces generated during rotation of the rotor 56 must also be taken into consideration in choosing the bearings 66.

The construction described together with a judicious choice of high quality bearings 66 will result in accurate tracking of the photometers during rotation of the rotor 56 thereby enable accurate and repetitively identical photometric measurements to be taken during operation of the apparatus. Notwithstanding precautions taken to assure accurate tracking and elimination of any eccentricity during rotation, the nature of the invention is such that some eccentricity during this rotation will not adversely affect accuracy as it would in the case of the type of apparatus disclosed in Greaves et al, above-mentioned.

The annular array of cuvettes 32 is mounted on the turntable 74 as explained. These may be removable cuvettes or the turntable may be molded or otherwise formed with the cuvettes 32 permanently attached thereto. The turntable 74 is journalled for rotation on the same axis 58 as that of the rotor 56 and the disposition of the turntable is above the rotor 56 so that access may be had to the entrances to the cuvettes 32 from above, as will be explained. The array of cuvettes extend downwardly from the body of the turntable 74 which is somewhat disc-like or planar in character, defining an annular ring path through which all of the cuvettes travel during rotation of the turntable 74. This ring intersects all of the radiation paths 54 of the photometers mounted on the rotor 56. These paths 54 are radially arranged about the rotor 56 and in the case of the very short paths 54 of the embodiments of FIGS. 2 and 3 the spaces between the filters 60 and the lamps 50 also define a similar ring that coincides with that formed by the path of cuvettes 32.

The photometers 50–52 can be mounted on the upper surface of the rotor 56 in any suitable manner by clamps or brackets or the like or could be mounted on the interior of a thickened disc forming the rotor which could be accurately molded to receive the same. In such case, a groove or trough or annular configuration could be formed in the upper surface of the rotor 56 in annular configuration to receive and clear the depending array of cuvettes during their rotation. The radiation paths could then be arranged to pass through the groove in a radial direction which will enable them to pass unobstructed through the walls of the cuvette where the aliquot being measured is located. The cuvettes are obviously made out of some transparent or translucent material and should have properly oriented walls that do not refract or scatter the beam of radiation passing through the same.

The cuvette turntable 74 has a hub with depending collar 76, is centered on the axis 58 and is journalled for rotation by means of bearings 78 that are mounted between the collor 76 and the sleeve 64, thus permitting the cuvette turntable to be rotated independently of the rotation of the photometer rotor 56. Rotation of the turntable 74 in an indexing mode can be effected by conventional means not shown in FIG. 3, but illustrated in FIG. 4 and discussed with respect thereto. Since the turntable 74 and the photometer rotor 56 are coaxial on the same axis 58, and the collar 76 of the turntable 74 rotates within the sleeve 64 of the rotor 56, the path of the cuvettes and the area swept by the photometers are concentric and the cuvettes are caused to intercept the short radiation path 54 of each photometer with highly reproducible positional accuracy thereby promoting accurate photometric measurements without need for complex light guiding arrangements employed in the prior art.

To enhance the continuously smooth rotary motion of the photometer rotor 56 it can be designed with weighted circumferential volume to operate with a flywheel effect. In contrast the cuvette turntable 74 should be relatively lightweight if the indexing thereof is to be accomplished in steps with dwell periods between steps.

FIG. 4 illustrates primarily a slightly modified arrangement of the photometer means 50–52. Such modification and other differences between FIGS. 3 and 4 will be presented after the discussion of FIG. 5, which includes explanation of most of the operation of the structure shown in both FIGS. 3 and 4.

As shown in FIGS. 3–5, the electrical output from the radiation detectors 52 is coupled to electrical components for analog to digital conversion and transmission from the data generating component assembly 34 to the control console 10 (FIG. 1). Preferably, the electrical components would be secured to portions of the rotor 56 and its sleeve 64, by way of circuit components, circuit boards and connectors such as 80 and 82, so that the electrical components can move along with their associated photometers, during their rotation around the axis 58, without the need for slip rings, commutators or the like at the sensitive points of the circuit or more complex wiring arrangements. The transmission of a large quantity of discrete electrical measurements in the form of analog values from a plurality of radiation detectors 52 that is continuously moving presents problems, both mechanical and electrical, which will be recognized by those skilled in the art. It is believed that the need for greater throughput of precise data from many photometers, concerning numerous chemical tests being carried out on a high number of aliquots, is not practically satisfied by the prior technology. The arrangement in FIG. 5 provides an efficient, flexible, yet simple and precise mode of data transmission.

Commencing with the top left of FIG. 5, there is shown one of the assemblies mounted on the rotor 56 which will be termed a photometer module 84 with its radiation source 50 directing its radiation to pass through the walls of one of the cuvettes 32 and strike the sensitive surface of the detector 52, after passing through the filter 60. The detector could be a silicon diode, a photomultiplier, vacuum photodiode or other photoresponsive device. A few milliseconds of scanning time by one of the photometers moving past an effectively stationary cuvette will be sufficient to obtain the required analog measurement of the radiation incident on the detector 52 to enable eventual calculation of absorption and absorbance. The detector 52 responds to the amount of radiation transmitted through the aliquot in the cuvette and the cuvette walls by generating an electric signal proportional to such amount of radiation. An integrator 86 is connected to the detector and converts the generated signal to an output voltage signal which is proportional to the transmittance of the aliquot. A logarithmic analog to digital converter 88 is coupled to the output of the integrator and generates as its output on a line 90 a digital signal which is a function of the absorbance of the aliquot. One example of a log A/D converter usable herein is set forth in Dorman et al U.S. Pat. No. 3,566,133. For ease of illustration, only one of the eight photometer modules 84 is illustrated, but all eight of the photometer output lines 90 are shown.

Since at one instantaneous position of the continuously moving photometer rotor 56 all eight of the detectors 52 could be respectively receiving radiation which has traversed the samples in eight different cuvettes, a digital multiplexer 92 is connected to all of the photometer output lines 90. The multiplexer operates in typical switching manner under the control of a data control unit 94, by way of a control line 96, discretely to transfer the data from each of the log A/D converters 88 to the data control unit on a data line 98. Such data can be handled in the form of binary bits, with one binary word representing the absorbance reading from one cuvette. The correlation of each specific absorbance data word with its aliquot or cuvette identification can be accomplished by the data control unit. The means for such identification and coupling same to data control unit are not illustrated and are within the skill of the art. After the data word has been transferred to the data control unit 94, that unit will generate a reset command on a line 100 to the appropriate log A/D converter 88 to enable that converter to receive the next analog signal derived from the next cuvette to be scanned by that one photometer 84.

Each integrator 86 will be reset by its A/D converter when its digital word is fed into the multiplexer. A reset line 102 carries that command, usually prior to the resetting of the A/D converter by the data control unit 94. To ensure that the radiation through one cuvette does not include radiation from an adjacent cuvette as seen by its integrator 86 the integrator can be enabled by a start integrate command line 104 which can be triggered in response to one of various conditions, such as: a timing relationship with the rotor drive means 72, or a positioning of the cuvette relative to the radiation path 54, or the shape of the output signal waveform from the detector 52.

Depending upon the sophistication of the data control unit 94 and the size of its memory, if any, the manner of data input-output handling can be variable. For example, by employing a simple data control unit, each instance that a digital word is fed into the data control unit it can be transmitted to the master control unit 20 and be processed therein for receipt by the readout unit 22. The master control unit can have a data storage and correlation capacity as well as the earlier mentioned function control, instruction and command information. On the other hand, if the data control unit has sufficient storage capacity, at least all data words such as the 960 mentioned which are obtained during one or more rotations of the rotor 56 can be stored therein.

Assuming that each of the photometers 52 is operating at a different wavelength and that a specific cuvette 32 is to be monitored by only the one photometer 52 operating at that wavelength which optimizes the measurement of the specific reaction occurring in that cuvette, then of the 960 data words received by the multiplexer 92 during one cycle or revolution of the photometer rotor 56, only one hundred twenty of those words (for the example described) normally would be needed by the master control unit 20. The determination of which data words are to be employed for data processing is developed from the input information which associates specific samples with specific tests. The master control unit 20 then assigns each specific cuvette to a sample and a test and thereby a specific photometer; whereupon, the data word required from that cuvette for each revolution of the rotor 56 can be identified and related to the data words from the same cuvette 32 obtained from each of the next following rotor revolutions, which in the preferred embodiment totals one hundred twenty revolutions of the photometer rotor 56.

Depending upon the desirable extent of communications between the data control unit 94 and the master control unit 20, the sizes of their memories, the speed of operation of the apparatus, etc., all of which involve cost, throughput and other factors which influence engineering design, the engineering design can cause all ninety six thousand words to be transmitted to the master control unit for its selection of the needed twelve thousand data words; or, the two control units 20 and 94 can communicate such that only the desired twelve thousand words are transmitted from the data control unit to the master control unit.

The engineering design is influenced by the timing of the transmission of the data words from the data control unit to the master control unit. There may be a finite amount of unused time between the scanning of each cuvette, while the rotor 56 is moving into alignment with the next set of eight cuvettes, and also at the end of each revolution, when the cuvette array is indexed one step. Since the apparatus can operate in the continuous mode, as earlier described, one revolution can be followed by the next without any significant disruption, as contrasted to the batch mode of operation. Hence, data also can be transmitted in a continuous mode and not stored until some later time and then dumped into a processing unit. This continuous transmission of data from the data generating component assembly 34 to the control console 10 may be with some control by the data control unit 94, rather than exclusively by the master control unit 20, as abovementioned.

In referring to unused time above, that is, time between the scanning of cuvettes or at the end of a revolution, no limitations on the invention are intended. Thus, it is feasible to measure dark current between cuvette scannings to set the photometer scales. The readings can readily be identified by the control unit and processed as desired and programmed.

Although a continuous operation mode has well known advantages over batch operation, there can be conditions which warrant batch handling. The apparatus of this invention can be used in batch processing. For example, the entire cuvette turntable 74 could be in the form of a removable disc to be replaced by one or more similar discs having the cuvettes already filled with aliquots and possibly even reagents, each replacement disc being a batch. If the batch would consist of only a few aliquots, the cuvette disc could be constructed in segments and then only a segment or portion of the disc be replaced with a prepared segment of cuvettes. Likewise, a stat or urgently needed test could be "inserted" into the apparatus.

Such a structure would have a turntable like that shown at 74 with a thin plastic disc, perhaps formed by vacuum molding a synthetic resin sheet with the depressions forming the cuvettes, capable of being clamped or snapped onto the upper surface of the turntable. The operation of the apparatus would not be too much different, being required only to enable proper orientation of the replaceable disc to provide sample identification and with some modification which starts and stops the apparatus so that the attendant may remove the used disc and replace it with a new one.

In normal operation such a disc or turntable would not be required to rotate and its cuvettes would be scanned by the plurality of photometers during rotation of the rotor 56. Stepping of the disc or turntable 74 would be useful where the apparatus could be alternated between continuous and batch modes. The removability of the disc on the turntable 74 could be of advantage where stat testing is to be done and it is not desired to integrate such tests in with the routine ones being processed. Stepping could also be of advantage along with removability in a batch mode where the steps carry different sets of filters into the radiation paths.

In a batch method device where the rotor carries a plurality of photometers, such photometers could employ individual lamps 50 for each photodetector 62 or a single central source of radiation serving all photometers.

One variation of the invention could comprise a fixed or indexing turntable with cuvettes and a rotor having a single photometer, but differing from the structure of DeMendez et al patent mentioned above in that the rotor also carries a filter wheel arranged vertically and intercepting the beam of radiation from the photometer before it passes through the cuvettes. The rotor in such case is arranged to stop momentarily at each cuvette and automatically rotate the filter wheel to provide several measurements at different wavelength that are identified by suitable synchronizing means to be sent to the proper address of the storage or recording device through data control means. In this way, the effect of plural photometers is achieved without the need for any duplication of photometers.

It is pointed out that the reference to the rotation or revolutions of the rotor 56 is not to be considered limited to movement in one direction since it is feasible for the rotor 56 to oscillate by rotating substantially one revolution and then reversing itself to rotate a revolution in the opposite direction, etc.

Next, with reference to FIG. 5, there will be disclosed both types of data flow and control; first, that which requires two-way communications between the control units 20 and 94; and second, one-way communications. The latter, although simpler than the former, would require more sophistication and also more storage capacity by the master control unit.

Two-way communications between the master control unit and the data control unit can be accomplished with the aid of a pair of communications logic units 106 and 108, a pair of transmitters 110 and 112, and a pair of receivers 114 and 116. The elements 106, 110 and 114 would be housed in the rotating portion of the data generating component assembly 34. The corresponding elements 108, 112 and 116 would be located in the control console 10 and/or a stationary portion of the assembly 34. A control bus 118 and a data bus 120 link the data control unit 94 with its communications logic unit 106.

In like manner, control and data buses 122 and 124 link the master control unit 20 with the communications logic unit 108. Typical of the bidirectional control information on the buses 118 and 122 would be the availability of one or more data words to be written into or read from one or the other or both of the memories in the units 20 and 94 and the availability of the associated logic unit 106 and 108 to receive or transmit such data.

Since in the now being described embodiment of the electronics there is to be two-way communications between the data control unit in the reaction table and the master control unit in the control console, the control and data buses 118-124 will be bidirectional as indicated by the arrowheads in FIG. 5. Also, the communications logic units 106 and 108 will possess two-way capabilities. A commercial form of such communications unit is the IM 6402 Universal Asynchronous Receiver—Transmitter of Intersil Corporation, Cupertino, California. Such unit can be used in the other communications embodiment to be disclosed subsequently.

The bidirectional data buses 120 and 124 will carry each data word serially in parallel bit order, but the inputs from the receivers 114 and 116 and the outputs to the transmitters 110 and 112 will be serially by bit. The preferred embodiments of the transmitters and receivers, as illustrated in FIGS. 3 and 5, respectively are photoemissive and photosensitive. FIG. 4 employs a slip ring assembly 110-116; however, other forms of transmission and reception are possible, such as of the radio frequency type, and are encompassed within the general terms and are not to be considered limited by the illustration of the preferred embodiments.

Phototransmission, as by a photodiode, is both simple and well suited to the handling of binary serial bit data and is well known to those skilled in the art. Moreover, photoemission and reception are less subject to interference than radio transmission, especially when the elements 110-116 can be closely spaced.

As shown in FIG. 3 the transmitter 110 and receiver 114 can be housed within the sleeve 64 and rotate therewith close to the axis 58. The associated elements 116 and 112 could be stationary and lie close to the projection of the axis 58 and be wired into the logic unit 108 in the control console 10. Mounted in such a manner close to axis 58, the fact that the transmitter 110 and receiver 114 are rotating will not cause errors in the binary bit data transmission. On the other hand, if the magnitude of a signal, rather than presence or absence thereof, were the measure of the test data and the control commands, then relative movement of the transmitters and receivers could produce transmission errors.

From the foregoing it will be appreciated that for economical use of storage capacity in the master control unit 20 only the desired data words should be transmitted from the data control unit 94. To effect such economy the input information from the data input means 18 will enable the master control unit to establish a listing of the aliquots or their cuvettes from which data is desired. As new samples are added to the sample disc 30, associated input information fed into the master control unit and old samples complete their testing the "desired" listing will by updated continuously. As each data word is received by the data control unit 94 from the multiplexer 92 it will, by two-way communications, be checked with the desired data list and only be transmitted to the master control unit after an affirmative comparison. This communication will require the data control unit and its logic unit to have interchanges on the buses 118 and 120 regarding: the fact that a data word has been received from the multiplexer, identification of that word and that the logic units 106 and 108 are ready to communicate that identification information to the master control unit.

In like manner, the master control unit and its buses 122 and 124 with its logic unit 108 will: acknowledge availability to communicate, receive the identification data, provide a comparison reply and then either cause the data word to be discarded by the data control unit or cause it to be transmitted for storage by the master control unit. Each communication will require transmission and receipt by one or the other pair of components 110 and 116, or 112 and 114.

In the other embodied form of data communications, all data words are transmitted from the data control unit 94 to the master control unit 20 and the latter then itself will decide which data words to continue to store for ultimate readout purposes. Because of this simpler form of communications the data buses 120 and 124 need only feed in the direction toward the master control unit, the communications logic unit 106 will operate only as a sending unit, the communications logic unit 108 will operate only as a receiving unit and the transmitter-receiver pair of elements 112 and 114 will not be required. The bidirectional control buses 118 and 122 between the control units and their respective communications logic units are required for the purposes above-mentioned.

The differences between the embodiments of FIGS. 3 and 4 will now be described. First, concerning the photometer means, the radiation source 50 of FIG. 4 is located at the axis 58 and comprises a single element such as a General Electric type 58 tungsten lamp rather than a plurality of lamps positioned around the periphery of the photometer rotor 56 as in FIG. 3. The source 50 in FIG. 4 is connected to the rotor 56 for rotation therewith.

A plurality of lens-containing optical tubes 126 are mounted to the photometer rotor 56 of FIG. 4 such that one end of each tube is proximate to the radiation source 50 and the other end of each tube is close to the annular path or pattern traversed by the cuvettes and is aligned with a specific one of the radiation or photometric detectors 52. The photometric detectors 52 are also mounted on the rotor 56 substantially as in the FIG. 3 embodiment. The paths or patterns swept by the beams of radiation reaching each detector is in effect the same as in FIG. 3.

One advantage of employing a single source 50 is that it is easier to dissipate the heat generated thereby and thus easier to regulate the temperature of the cuvettes 32. Note that in the embodiment shown in FIG. 3 the individual lamps are located quite close to the annular ring defined by the cuvette path so that the heat of these lamps could be radiated or transmitted to the materials carried by the cuvettes. The nature of many of the reaction whose characteristics are being measured is such that temperature changes are critical. As a matter of fact, means will often be provided for incubation of the cuvettes during their scanning and the arrangement of FIG. 4 enables such structure to be easier achieved and more effective in operation because of the absence of heat sources.

Another advantage of a single source such as in FIG. 4 is that there is no problem with different intensities, colors or wavelengths which can be expected in a plurality of different lamps, even where matched. Whatever happens to the single source lamp 50 happens to all readings made so that the effect is not felt where relative measurements are made. The lamp 50 can be cooled very easily by air circulated in its vicinity in a manner which will not cool, for example, the cuvettes. The power supply for a single source 50 is simpler and more economical.

In the views described thus far shown there is a single beam 54 which passes through the cuvette 32 and thence impinges upon the photodetector 52 after passing through a filter 60 which is usually in close proximity if not incorporated into the photodetector. In the structure of FIG. 4 it is feasible to focus the light beam into a very fine pencil for passage through the lower portion of the cuvettes 32 but in addition it is feasible to incorporate beam splitting means into the focussing tube or outside thereof to provide two beams which may be directed in parallel paths through different levels of the cuvettes for investigating different strata of the analyte. Such a structure is shown in FIG. 4a to be described in detail below.

Figure 4A:
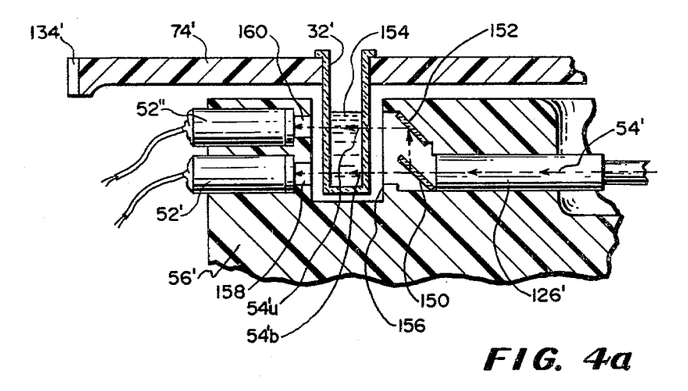
FIG. 4a is a fragmentary view of a portion of FIG. 4 but illustrating a modified form of the invention utilizing a split beam arrangement.

In FIG. 4a components equivalent to those of FIG. 4 carry the same reference numerals primed. The rotor 56' has a focussing tube 126' which directs a beam 54' derived from a source such as 50 (not shown in FIG. 4a) to a semisilvered or dichroic mirror 150 arranged at 45° in front of the tube 126'. A part of the beam passes through the mirror 150 and becomes a bottom beam 54'b and another is reflected at 90° upward and thence reflected from the 45° angled mirror 152 to become the upper beam 54'u. These beams pass through different levels of the liquid 154 carried in the cuvette 32' mounted in the turntable 74' which is disposed to move in a path which carries it and its companion cuvettes through the groove 156 provided in the rotor 56.

There are two photodetectors at 52' and 52" mounted on the rotor 56 in suitable cavities aligned with the mirrors 150 and 152, respectively, and thus aligned to receive the beams 54'b and 54'u against their sensitive surfaces. Each is provided with a filter 60' and 60", respectively. Openings 158 and 60 respectively enable the beams to pass.

It will be obvious that the beam 54' emerging from the focussing tube 126' splits, part going through a lower stratum of the liquid 154 and part going through an upper stratum of the same liquid. The photodetectors 52' and 52" are independent, each providing a different signal which can be transmitted through suitable connections to data processing equipment to provide additional information concerning the reaction which may be going on in the cuvette 32'.

FIG. 4 shows the drive means for the cuvette turntable 74, which was not illustrated in FIG. 3, because of drawing space limitations. A motor 128 has its drive shaft 130 coupled by a pinion gear 132 to a suitably mating configuration 134 on the periphery of the turntable 74. If the indexing of the cuvettes is to be in steps, the motor 128 could be a stepping motor, or there could be provided linkage, clutch means, etc., for providing appropriately timed stepping from a continuously driven motor.

As earlier mentioned briefly, a slip ring assembly 110-116 can provide the receiver and transmitter needs of the apparatus and couple data and other communications from and to the reaction table 34 and the master control unit 20. Such slip ring units are available commercially.

From the above, it now should be understood how the entire apparatus operates with its moving photometer means and preferably in a continuous mode to place into the master control unit 20 the digitized values of the readings related to absorbance from the data generating components assembly 34. Since reaction can be monitored at frequent intervals during a prolonged period of time rather than a small portion thereof, both rate and end point data are obtainable. Once into the master control unit, the raw data can be associated with each test and supplied to the readout unit 22 without any data reduction, conversion or analysis, such being left to the skill of a technician in interpreting the same. In a preferred mode of operation the master control unit would have the capability of associating the data for each test, obtaining mathematic rate and/or end point determination, then converting that information into a reading of the chemistry value in the desired concentration units for the test, thereafter feeding the results into the readout unit.

Although some variations in structure and operation of this chemical reaction monitoring apparatus have been disclosed hereinabove, other variations are capable of being made by those skilled in the art without departing from the spirit or scope of the invention as defined in the appended claims. For example, the preferred embodiments teach continuous movement of the photometer rotor; however, a stepping device movement can be employed. Also, the photometer means are spaced around the circumference of their support, since such positioning enables a uniform weight distribution around the support; however, the photometer means could be mounted with variable spacing especially if the path of motion is other than circular. It may be desired to employ disposable cuvettes. If so, the laundry station 48 would be replaced by means for removing used cuvettes and for inserting clean cuvettes into the cuvette turntable 74. At least in such situation, the cuvettes need not move around a closed path. Reagents need not be liquid but may dispensed dry. Cuvettes may be used in a disposable mode with the reagent already in place, requiring only the addition of the aliquot and a diluent.

What it is desired to secure by Letters Patent of the United States is:

1. Apparatus for monitoring chemical reactions occurring in a plurality of liquid or the like sample substances carried in a plurality of respective cuvettes whose walls are at least to some extent capable of transmitting radiant energy which comprises:

A. support means,
   B. a rotor mounted on said support means for rotation thereon on an axis,
   C. a turntable mounted coaxially with the rotor for rotation relative to said support means, a plurality of radiant-energy-transmissive cuvettes mounted to the turntable and disposed in a circular arrangement coaxially with said axis and adapted to have sample substances producing chemical reactions carried in at least some of said cuvettes,
   D. first drive means for rotating the turntable on its axis in a first program of rotation whereby the cuvettes describe an annular path as the turntable rotates,
   E. second drive means for rotating the rotor on said axis in a second program of rotation in which the number of total revolutions of the rotor for a given period of time is greater than the number of revolutions of the turntable for the same period of time,
   F. photometer means mounted on the rotor and defining at least one beam path for radiant energy which extends at least through said annular path such that the beam path includes and traverses at least a portion of the sample substance which may be contained in any of said cuvettes which intersects such beam path during rotation of the turntable,
   G. the photometer means including means responsive to any radiant energy projected along said beam path to produce electrical signals as the cuvettes intersect the beam path, which signals are related to chemical conditions of the sample substances, if any, which may be contained in said cuvettes, there being two radiant energy detectors and means for dividing the beam path into two parts and directing the parts through different strata of the cuvettes,
   H. means for generating usable data from any such signals, and
   I. means for coupling at most all of the electrical signals from said photometer means to said data generating means.

2. In apparatus for monitoring chemical reactions, a plurality of cuvettes adapted to have respective liquid or the like samples contained therein, the chemical reaction of which it is desired to monitor, photometer means including a beam path for radiant energy adapted to intersect and pass through all of the cuvettes to provide respective electrical signals related to the chemical reactions occurring in the respective cuvettes, and means for generating data based upon and responding to said signals, the invention comprising photometric detector means constructed and arranged as part of the photometer means for generating the electrical signals and also means to cause movement of both said cuvettes and photometer means relative to each other and also relative to a reference location, said movement means comprising:

first movable carrier means having the photometer means mounted thereon and arranged to cause the beam path to trace a certain first repetitive pattern during movement thereof, second movable carrier means having the cuvettes mounted thereon and arranged to cause the cuvettes to trace a certain second repetitive pattern during movement thereof, said first and second movable carrier means both having drive means for their independent moving, the first and second repetitive patterns being geometrically related to one another such that there is a signficant portion of each which coincide, such that when the photometer means moves through said significant portion it will scan the cuvettes which are simultaneously located thereat and the photometric detector means will generate the related electrical signals, the speed of movement of the first carrier means being substantially greater than that of the second carrier means to an extent that each cuvette moving through said coincident portion will be scanned at least once by said beam path during its presence in said coincident portion, said photometer means including means providing an output proportional to the transmittance of the contents of each cuvette scanned, photoemissive transmitter and photoresponsive receiver means coupled to receive said output, said transmitter means being mechanically connected for movement along with said photometer means and said receiver means being stationary, said first movable carrier means being movable about an axis and said transmitter means being mounted proximate to said axis, a plurality of photometric detectors being mounted to the said first movable carrier means, each photometric detector providing its own digital output, and output routing and control means by which said digital output is associated with respect to the originating cuvette, and a chemical reaction test result is obtainable for each cuvette.

3. Apparatus according to claim 2 in which said output routing and control means have one portion mounted for movement with said photometer means carrier means and is coupled between said photometric detectors and said transmitter means, and there is another portion of said output routing and control means which is coupled to said receiver means, is stationary and includes a master control unit.

4. Apparatus according to claim 3 in which additional transmitter means are coupled to said another portion and transmit to additional receiver means that are coupled to said one portion and are movable therewith for establishing two-way communications between said portions.

5. Chemical reaction monitoring apparatus comprising:
A. cuvette carrier means,
B. photometer carrier means,
C. a plurality of photometers mounted on the photometer carrier means and including a detector for each photometer and source means of radiant energy also mounted on the photometer carrier means projecting an energy beam to each said detector,
D. the cuvette carrier means adapted to have at least one radiant-energy-transmissive cuvette carried thereby and said cuvette adapted to have a liquid sample contained therein to enable a condition of chemical reaction therein to be monitored,
E. means for moving the cuvette carrier means and the photometer carrier means in a repetitious cycling movement relative to one another so that each beam intersects and passes through said cuvette repeatedly once each cycle,
F. means for generating signals relating to said condition and responsive to the outputs of said detectors,
G. means for acquiring usable data from said signals and,
H. said signal generating means including A/D conversion circuitry carried on said rotor and rotating therewith.

6. The apparatus as claimed in claim 5 in which said A/D conversion circuitry is connected with each photometer carried on said rotor and rotating therewith.

7. Apparatus for measuring the absorbance of chemical reactions occurring and/or occurred in a plurality of liquid or the like sample substances carried respectively in a plurality of cuvettes which comprises:
A. a support structure,
B. a horizontally disposed cuvette carrier having a plurality of cuvettes disposed thereon in a circular array about a central vertical axis, the cuvette carrier being mounted on the support structure, the cuvettes having walls capable of transmitting radiant energy,
C. a rotor horizontally disposed parallel with the cuvette carrier and mounted for rotation on said axis,
D. a photometer secured to said rotor and including a source of radiant energy of a type which said cuvettes are capable of transmitting, a photoresponsive element aligned with the source of radiant energy and adapted to receive a beam of radiant energy emerging from said source, the source and photoresponsive element being arranged such that the beam lies on a radius of the rotor with one of the element and source located inside the circular array and the other of said element and source located outside of said circular array, the rotation of the rotor causing the beam to describe a locus which is an annular disc,
E. the vertical relationship between the array of cuvettes and the locus being such as to cause the disc to intersect the cuvettes at a level where sample substances carried thereby will be traversed by the beam,
F. means for driving the rotor in a rotary movement to cause the beam to intersect all of the cuvettes in sequence, at least once for each revolution of the rotor if the rotor is rotated more than one revolution relative to said array and a proportionally lesser number of times if the rotor is rotated less than a revolution relative to said array, G. the photoresponsive element being responsive to said beam to produce an analog signal, the signal resulting when the beam passes through a cuvette being related to the transmittance of said cuvette plus the sample substance, if any, carried by said cuvette, H. means for producing data on the absorbance of the substances through which the beam has passed during rotation of the rotor, said data producing means being associated with the support structure, being nonrotatable and being responsive to digital information, I. an A/D converter carried on said rotor and connected with the photoresponsive element for converting the analog signals generated by said photoresponsive element into digital information and J. coupling means including a fixed portion carried by said support structure and a rotary portion secured to said rotor, the rotary portion being connected to the A/D converter to receive the output thereof and the fixed portion being connected to said data producing means.

8. The apparatus as claimed in claim 7 in which the coupling means comprise a slip ring device located at said axis.

9. The apparatus as claimed in claim 7 in which the cuvette carrier is also mounted for rotation on said axis and drive means are provided to rotate said carrier slower than the rotor.

10. Apparatus for monitoring chemical reactions occurring in a plurality of liquid or the like sample substances carried in a plurality of respective cuvettes whose walls are at least to some extent capable of transmitting radiant energy which comprises:

A. support means,

B. a rotor mounted on said support means for rotation thereon an axis,

C. a turntable mounted coaxially with the rotor for rotation relative to said support means, a plurality of radiant-energy-transmissive cuvettes mounted to the turntable and disposed in a circular arrangement coaxially with said axis and adapted to have sample substances producing chemical reactions carried in at least some of said cuvettes, D. first drive means for rotating the turntable on its axis in a first program of rotation whereby the cuvettes describe an annular path as the turntable rotates, E. second drive means for rotating the rotor on said axis in a second program of rotation in which the number of total revolutions of the rotor for a given period of time is greater than the number of revolutions of the turntable for the same period of time, F. said photometer means are mounted on said rotor and comprise a plurality of photometers spaced about said rotor circumferentially, each photometer having structure defining a beam path for radiant energy disposed radially relative to the axis of said rotor such that all beam paths will extend through said annular path and the cuvettes will intersect all of the beam paths as said rotor rotates and each beam path will traverse at least a portion of the sample substance which may be contained in said cuvettes during rotation of said rotor, G. each photometer including independent means responsive to its radiant energy beam projected along its respective path to produce electrical signals as the cuvettes pass through the beam, which signals are related to chemical conditions of the sample substances, if any, with regard to all of the beam paths, said means to produce electrical signals of each photometer include an analog to digital converter, H. means for generating usable data concerning the absorbance of the sample substances from any such signals, said data generating means comprising the following elements in series connection: a digital multiplexer having its inputs coupled to the output of each said converter, means for presenting the digital data concerned with absorbance into serial bit order, and data bit transmitter means, such elements being mounted to said rotor, and said data generating means further comprising the following elements structurally mounted to said support means and connected in series: a data bit receiver, series bit to parallel bit order logic communication means, and a master control unit, and I. means for coupling all of the electrical signals from said photometer means to said data generating means.

11. The apparatus as claimed in claim 10 in which the data generating means comprise at least a computing device and the coupling means include receiving structure carried on the support means and providing a fixed communication link between the computing device and the photometers and transmitting structure carried on the rotor and providing a rotating communication link between the computing device and the photometers.

12. Apparatus for monitoring chemical reactions occurring in a plurality of liquid samples carried in a plurality of respective cuvettes which comprises:

A. support means,

B. a generally planar carrier mounted on said support means and having a plurality of radiant-energy-transmissive cuvettes disposed thereon in a generally circular array and adapted to have liquid samples producing chemical reactions respectively held in said cuvettes, each cuvette having a portion freely protruding from said carrier and all cuvettes thereby defining an annular ring projecting from said carrier, C. a rotor mounted on said support means for rotation on an axis which coincides generally with the center of said circular array and there being drive means for rotating the rotor in a movement parallel to the plane of the carrier, D. a plurality of photometers mounted on the rotor and each being radially arranged relative to the axis and including source means of radiant energy and a radiant-energy-responsive element spaced apart whereby to define a beam path therebetween, including at least an A/D converter connected to each photometer to process said electrical signals of the radiant-energy-responsive element of said photometer mounted on the rotor, E. the rotor and carrier being arranged in proximity so that the annular ring is located in the beam paths whereby during rotation of the rotor each beam path will be intercepted by substantially all cuvettes for each rotation of the rotor, F. the radiant-energy-responsive elements adapted to generate electrical signals respectively related to the absorbtivity of the liquids, if any, contained in the cuvettes which intercept the said beam paths during rotation of said rotor, G. means for generating usable data from said signals relating to the chemical reactions, if any, in the respective cuvettes, and H. means for coupling the electrical signals from the rotating photometers to said data generating means.

* * * * *

UNITED STATES PATENT AND TRADEMARK OFFICE
CERTIFICATE OF CORRECTION

PATENT NO. : 4,234,538
DATED : Nov. 18, 1980
INVENTOR(S) : Ginsberg et al

It is certified that error appears in the above-identified patent and that said Letters Patent are hereby corrected as shown below:

In the abstract

Line 15 - the second occurrence of "that" should be omitted;

column 9, line 41, the second occurrance of "be" should be omitted;

column 14, line 15, "wave lengths" should read -- wavelengths-- column 15, line 39, "by" should read -- be --;

column 16, line 35, "reaction" should read -- reactions -- and column 21, line 41, (claim 10, line 8, -- on -- should be inserted after "thereon".

Signed and Sealed this

Fifth Day of May 1981

[SEAL]

Attest:

RENE D. TEGTMEYER

Attesting Officer    Acting Commissioner of Patents and Trademarks